United States Patent [19]
Grim et al.

[11] Patent Number: 5,645,426
[45] Date of Patent: Jul. 8, 1997

[54] DENTAL PROPHY ANGLE

[75] Inventors: Carlton L. Grim, Red Lion, Pa.; David B. Schumaker, Morristown, Tenn.

[73] Assignee: Dentsply Research & Development Corp., Milford, Del.

[21] Appl. No.: 534,811

[22] Filed: Sep. 27, 1995

[51] Int. Cl.⁶ .................................................. A61C 3/06
[52] U.S. Cl. .................................. 433/125; 433/134
[58] Field of Search .............................. 433/125, 126, 433/133, 166, 134

[56] References Cited

U.S. PATENT DOCUMENTS

| | | | |
|---|---|---|---|
| 794,006 | 7/1905 | Gossling | 433/126 |
| 2,090,885 | 8/1937 | Clark | 433/133 |
| 2,451,192 | 10/1948 | Blair | 433/133 |
| 3,727,313 | 4/1973 | Graham . | |
| 3,740,853 | 6/1973 | Brahler . | |
| 5,040,978 | 8/1991 | Falcon et al. | 433/125 |
| 5,120,220 | 6/1992 | Butler | 433/126 |
| 5,156,547 | 10/1992 | Bailey | 433/125 |
| 5,328,369 | 7/1994 | Bailey | 433/125 |
| 5,348,473 | 9/1994 | Kivlighan, Jr. | 433/114 |
| 5,352,119 | 10/1994 | Sahurai | 433/126 |
| 5,423,679 | 6/1995 | Bailey | 433/125 |

*Primary Examiner*—Cary E. O'Connor
*Attorney, Agent, or Firm*—James B. Bieber

[57] ABSTRACT

A prophy angle having a single improved snap-in mounting shaft having an enlarged snap-through outer boss portion that is discontinuous in circumference for retaining the prophy cup rotor in permanent position and isolating the rotor from frictionally engaging other parts other than through the gearing except under stress, a press fit drive shaft retention locking sleeve that frictionally engages the housing when pressed into locking position, a reduction of the surface contact of the drive shaft with the inside of the housing by introducing vanes in contact with the housing wall rather than a continuous cylinder contact, and a closed vent hole with a hub on the drive shaft.

9 Claims, 3 Drawing Sheets

DENTAL PROPHY ANGLE

BACKGROUND OF THE INVENTION

This invention relates to dental prophylaxis angles and more especially to those to be thrown away after each patient to avoid cross infection.

The present application is specifically directed to improvements in the prophy angle shown in U.S. Pat. No. 5,040,978. These improvements may however be applicable to other prophy angles. There are in the market a number of disposable prophy angles some of which are represented by the disclosures of U.S. Pat. Nos. 3,727,313; 3,740,853 and 5,423,679. It is recognized that making reasonably inexpensive but reliable prophy angles enables the dental professional, dentist or hygienist, to use a prophy angle for a complete prophy of one patient and then discard the prophy angle rather than sterilizing the angle. Sterilization is not only expensive in time and equipment but means handling the contaminated prophy angle.

To reduce cost prophy angles have been constructed of plastic. Plastic has not provided the rugged construction and reliability of steel, but with innovative construction techniques usable inexpensive angles have been provided.

It is an object of the present invention to provide improved disposable prophy angles.

It is a further object to provide prophy angles that can be manufactured less expensively.

It is a yet further object of the present invention to provide prophy angles that give superior performance with greater reliability.

It is another object of the present invention to provide prophy angles that give smooth, even and consistent performance not only during a prophy treatment of a patient but from one prophy angle to the next so dental professionals will have the same "feel" from one prophy angle to the next prophy angle as they treat a series of patients.

SUMMARY OF THE INVENTION

By an aspect of the invention an improved solid stud with an enlarged head that has cut outs or indentations into its sides is provided allowing the edges of the enlarged head to bend down without having to compress or fold the material circumferentially. This enables the expeditious forcing of the enlarged head through a hole commensurate with a strong sturdy stud.

Another aspect of the invention is the reduction of friction by constructing and sizing the parts adjacent to the rotor so that during free running only the journal mounting of the stud and the meshed gears frictionally engage the rotor.

A further aspect of the invention is reducing friction and increasing reliability by eliminating flexing parts that can break in the mounting of and operation of the long driving gear by securing the gear in position with a press fit locking sleeve and reducing the length of the cylinder of the long gear while retaining stabilizing length of supporting engagement contact with the inside wall of the housing bore through vanes which reduce the area of contact and yet provide the needed support against buckling and breaking and maintaining the desired length in the housing to properly position the dental prophy cup or other tool.

By yet another aspect of the present invention the vent hole and hub of the long gear are so positioned that the vent hole is closed to the inside of the housing substantially solving a pumping problem inherent when rotating gears and parts have an inlet and outlet through which a fluid (gas, saliva, debris, and water) can flow in a stream passing through the housing.

DESCRIPTION OF THE PREFERRED EMBODIMENTS

Figure 1:
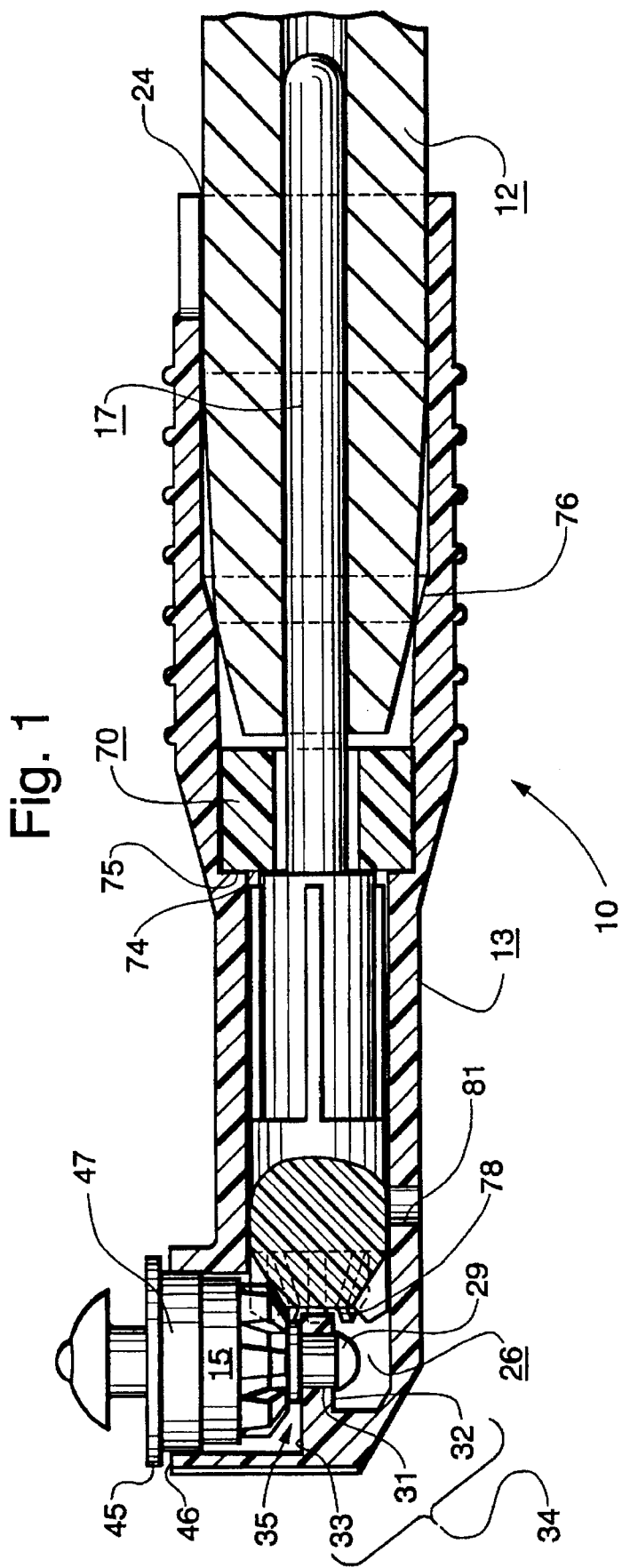
FIG. 1 is a substantially central longitudinal sectional view through a prophy angle of the present invention.

Referring first to FIG. 1 of the drawings, one preferred embodiment 10 of the prophy angle of the present invention is shown. The nose 12 of a powered dental handpiece of conventional type is also shown.

A housing, 13 is preferably molded as a single integral unitary unit from plastic. By integral unitary, it is meant that the housing is not an assembly of parts welded together or otherwise interconnected, but a single continuous piece of plastic manufactured as a unitary molded part. Looking also at FIG. 2, the gross housing 13 provides a housing 14 for a prophy cup mounting or rotation member rotor 15 and a housing 16 for an elongated drive shaft 17. The housing 14 has a passageway 20 with a central axis that intersects the central axis of a passageway 21 in the housing 16 at an angle. While the intersecting angle is shown as a right angle and a right angle is preferred in most embodiments, in some embodiments other intersect angles may be preferred.

The housing 14 and its passageway 20 have an outer open end 22 opening out from the gross housing 13 and an inside, inner or inward end with an inner opening 23. The housing 16 and its passageway 21 also have an open end 24 opening out from said gross housing 13 and an inside, inner or inward end with an inner opening 25 which opens into and joins with passage 20. The confluence of passageway 20 and passageway 21 form a mounting and connection section 26 of the gross housing 13. The inner end of the passageway 21 has a bore 28 of predetermined inside circumference, having a diameter as shown of 0.276 inch +0.003, −0.000 inch, defined by its wall of housing 16.

The housing 14 has an attachment retainer 27 that is an integral unitary part of the housing in the form of a strut or shelf. The rotor or prophylaxis tool mounting member 15 has an end mounting attachment member 29 (FIG. 2) in the form of a projection or assembly attachment mounting shaft at one end engaged with the attachment retainer 27 (FIG. 1). In this manner the rotor 15 is attached with and mounted and retained in secured position by the housing 14 in operable position.

The attachment retainer strut 27 is preferably a shelf-like bracket structure that for purposes of expeditious injection molding and function is wholly contained in passageway 20 but is aligned with passageway 21. The strut 27 extends out from the inside of housing 14 which is part of gross housing 13 in the mounting and connection section 26 of the gross housing 13. The strut is aligned with the outer opening 24 of the passageway 21 and has a hole or mounting passageway 31 (FIGS. 2 and 3) therethrough aligned with the central axis of the second passageway 20. The strut 27 has a flat retaining surface inner mounting bearing 32 opposite the outer opening 22 of the second passageway and adjacent the hole 31. The opposite face of the strut is a retainer and position fixing flat surface outer mounting bearing 33. The hole forms the shaft bearing 31 and with oppositely facing bearing surfaces 32 and 33 forms a mounting bearing 34 fixing and maintaining the position of rotor 15 during operation of the prophy angle 10. While the bearing faces are shown as flat it will be understood that in some configurations they may not be smooth. Webs 37 (FIG. 2) are strengthening structure and there are two more spaced at each side of the strut 27 to add strength against flexing or breaking.

From the above it may be seen that the dental prophylaxis angle 10 has a journal mount 35 composed of the journal parts 34 of the strut or shelf 27 and the journal parts 43 of the rotor 39. The mounting journal parts 34 include the hole shaft bearing 31 in the strut 27, a flat retaining surface inner mounting bearing surface 32 of the strut 27 and the position fixing flat surface outer mounting bearing surface 33 of the strut 27. The rotor or tool member mounting journaled parts 43 include the journal shaft 40 engaged in the mounting hole shaft bearing 31, the inner thrust bearing 42 engaged with the inner mounting bearing 32 and the outer thrust bearing 41 engaged with said outer mounting bearing 33. These engaged members are spaced in engagement with tolerances of between about 0.003 to 0.011 and 0.008 to 0.050, allowing for free rotation of the tool mounting member while holding it in position without positioning engagement with other structure except when significant side moment pressure is encountered by a tool mounted thereon.

Figure 3:
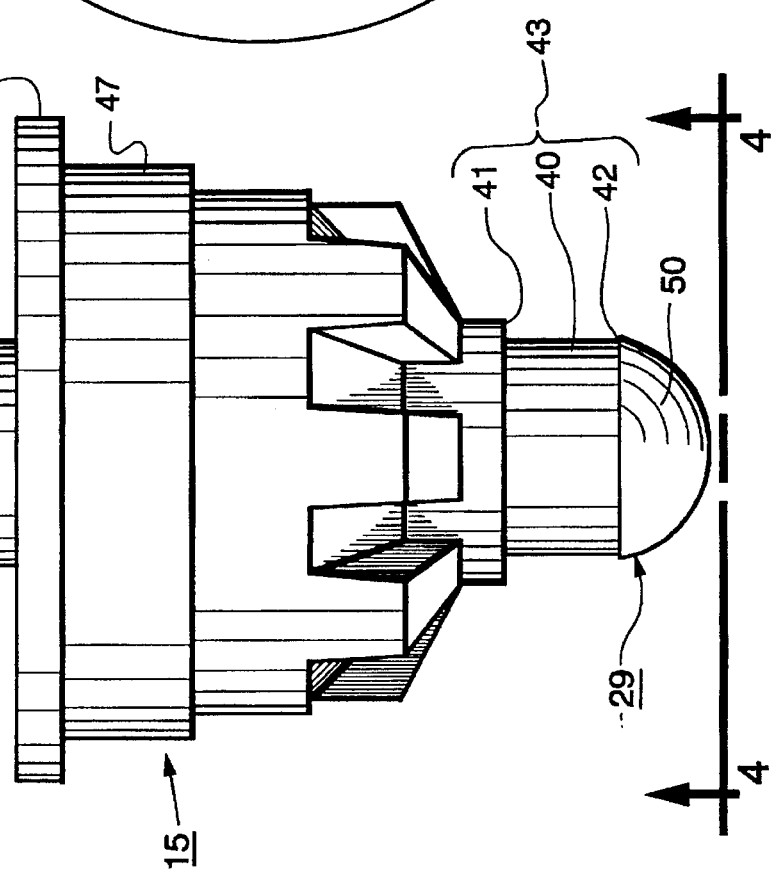
FIG. 3 is an enlarged elevational view of the rotor 15 of FIG. 2.

Looking at FIGS. 1 and 3 it will be understood that the mounting attachment member 29 of rotor 15 is a mounting shaft 29 which has a journal shaft portion 40 separating two journaling thrust bearings, outer journal thrust bearing 41 and inner journal thrust bearing 42 and these three elements form the journal 43. The thrust bearings are spaced apart with enough tolerance to allow free rotation without binding when mounted on the mounting bearing 34.

An important feature of the present invention in one of the invention's aspects is the manner of mounting the rotor 15 in the housing 13 which substantially isolates or limits the predominate frictional impediment to free rotation to the journal mount 35 which is composed of the mounting bearing journal parts 34 of the strut 27 and the journal parts 43 of the rotor 15. The shaft 29 is journaled in bearing 34 of the attachment retainer 27. The journal mount 35 is the sole means retaining the tool mounting member 15 in the housing 14 and the predominate centering means. This is accomplished by sizing the parts so that when the rotor 15 (looking at FIGS. 1, 2 and 3) is mounted, the flange 45 of rotor 15 overlays and is spaced from the outer edge or end face 46 of the outer open end 22 of passage 20 of housing 13 and the circumference of centering cylinder 47 is sized sufficiently smaller than the inner circumference of the bore of the outer open end 22 so that there is no touching or frictional engagement between either end face 46 and flange 45 or cylinder 47 and the inside of bore 20 when the rotor 15 is centered. These spacings are however, close enough to provide even rotational steadying should any rotational wobbling occur during operation and to hold the rotor in substantially centered position in the bore 20 when side pressure is exerted during operation of sufficient moment to flex the parts to the side inside the bore. Only under these circumstances should this centering cylinder engage the walls of the bore. The sizing preferably provides a space of about 0.001 to 0.004, more preferably 0.001 to 0.002 inch per side. The space between the flange 45 and the outer face 46 of passageway 20 is about 0.002 to 0.008, more preferably 0.002 to 0.003 inch.

The flange 45 of the rotor 15 is remote from the shaft 29 and a driven gear 80 is between them. Only the journal 43 and the driven gear 80 are frictionally engaged when the dental prophylaxis tool mounting member 15 is operated and the tool is unengaged.

Looking at FIGS. 1, 2, 3 and 4, another important feature of the present invention in one of its aspects is shown. The outer end of the end mounting attachment member 15 is formed in a manner that allows its insertion through hole 31 in strut 27 with only acceptable resistance and holds against the extraction of the shaft 29 from the bearing provided by the walls of the hole 31 and the bearing faces 32 and 33 that face outwardly from the surfaces of the strut 27.

The enlarged portion or boss 50 at the outer end of the shaft 29 in a preferred configuration has an oval shape, being shorter in direction 50b and longer in direction 50a. The two opposed lobes together form a substantially even oval in a plane perpendicular to the axis of the shaft 40. The oval preferably has a diameter substantially equal to the diameter of the journaled shaft portion at the ovals narrowest dimension. Preferably each opposed lobe projects 0.0045 to 0.008, more preferably 0.005 to 0.0075 inch from the circumference of the shaft at the lobes greatest extension. The ovals diameter at the narrowest diameter is preferably equal to the journal shaft diameter, which is about 0.088 to 0.090, more preferably 0.0885 to 0.0895 inch. The outer end of the shaft 29 is substantially evenly curved and is substantially a half circle taken in cross section at its greatest projection. The journal shaft 40 circumference is shown in phantom line.

The boss 50 is sized to require forcible insertion through the bearing hole 31 when the tool mounting member rotor 15 is mounted. As the boss 50 is forced through it distorts due to slight resiliency and its sloping outer face camming surfaces cam down the edges or extended projecting ends 51 and 52 that extend laterally away from shaft 40 and beyond the dimensions of the hole 31. This aids in passage through the bearing hole 31. The edges then rebound or pop out above the face or bearing surface 32 of the strut 27. Because the inside retaining thrust bearing face or surface 42 of the boss is not tapered toward the hole 31 but is substantially parallel in extension to the bearing face 32 the rotor is permanently retained in position for operation.

The retaining surfaces 42 on the rotor are in mating engagement with the retaining surfaces 32 with the projecting portions 51 and 52 projecting laterally beyond the circumference of the journal shaft 40 and the hole 31 circumferentially adjacent thereto. While as shown in a preferred embodiment there are only two lateral extensions that oppose one another circumferentially there could be three or more lateral extensions but preferably they would be evenly spaced circumferentially to balance the camming forces of the camming surfaces to help pass the outer end of the mounting attachment member 15 through the hole 31, substantially aiding in alignment and maintaining the alignment of the tool mounting member with the axis of the open end 20 as the enlarged portion 50 is forcibly inserted through the hole 31 in the strut 27.

Figure 4:
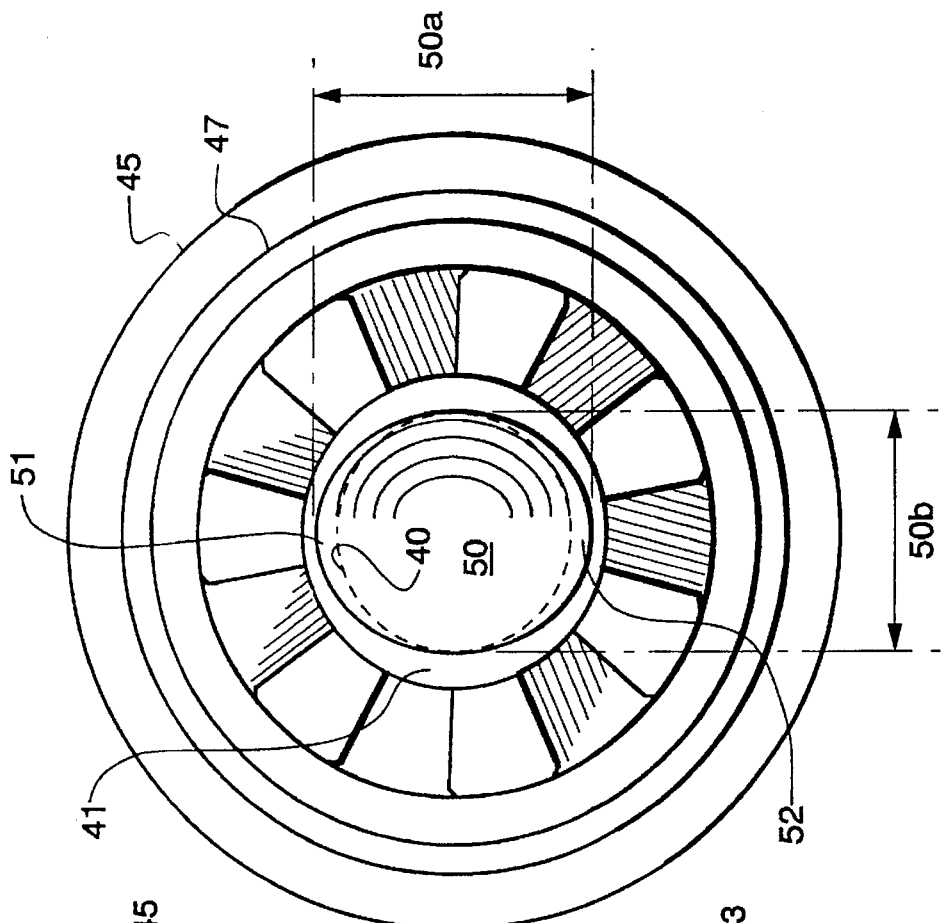
FIG. 4 is a end elevational view at line 4—4 of FIG. 3.

The oblong shape of the boss 50 in plan view as shown in FIG. 4 allows the stiff plastic to bend more easily because it does not also have to fold to reduce its circular dimension. This provides a much stronger and less brittle end mounting attachment than previously employed where a slot and hollow core in the shaft were found desirable to facilitate passage of a substantially ridged plastic shaft member through a bearing hole in a mounting strut such as is shown in U.S. Pat. No. 5,040,978. It is surprising that good even performance can be obtained with only the limited extraction retardent bearing face areas that provide only the two oppositely projecting extensions 51 and 52 from the inner shaft 40. In this regard the bearing hole 31 has a diameter of preferably 0.091 to 0.094, more preferably 0.091 to 0.092 inch.

The boss 50 in other preferred embodiments could have a shape other than the most preferred, even oval. In some instances an uneven oval or another cut out configuration such as squared off fingers will be preferred. Also the inner most projecting tip of the boss in other preferred embodiments will not be the most preferred rounded part of a circle configuration, but another configuration such as a frustaconical shape or other wedge shapes or in some embodiments yet other shapes and in some the resiliency of the plastic will need to be varied or the length of the projections varied. The term inner refers to inwardly into the housing 13. An advantage of following the more preferred embodiments of the present invention is the stronger solid mounting shaft 29 with the cut outs in the inner thrust bearing 42 lessening the mass and area of contact with the inner mounting bearing surface 32 reducing friction, drag and heat. This enables the push through capability with acceptable assembly pressure requirements and no compromise in plastic strength or brittleness, resiliency of the plastic need not be increased, which gives rigidity during operation.

Figure 2:
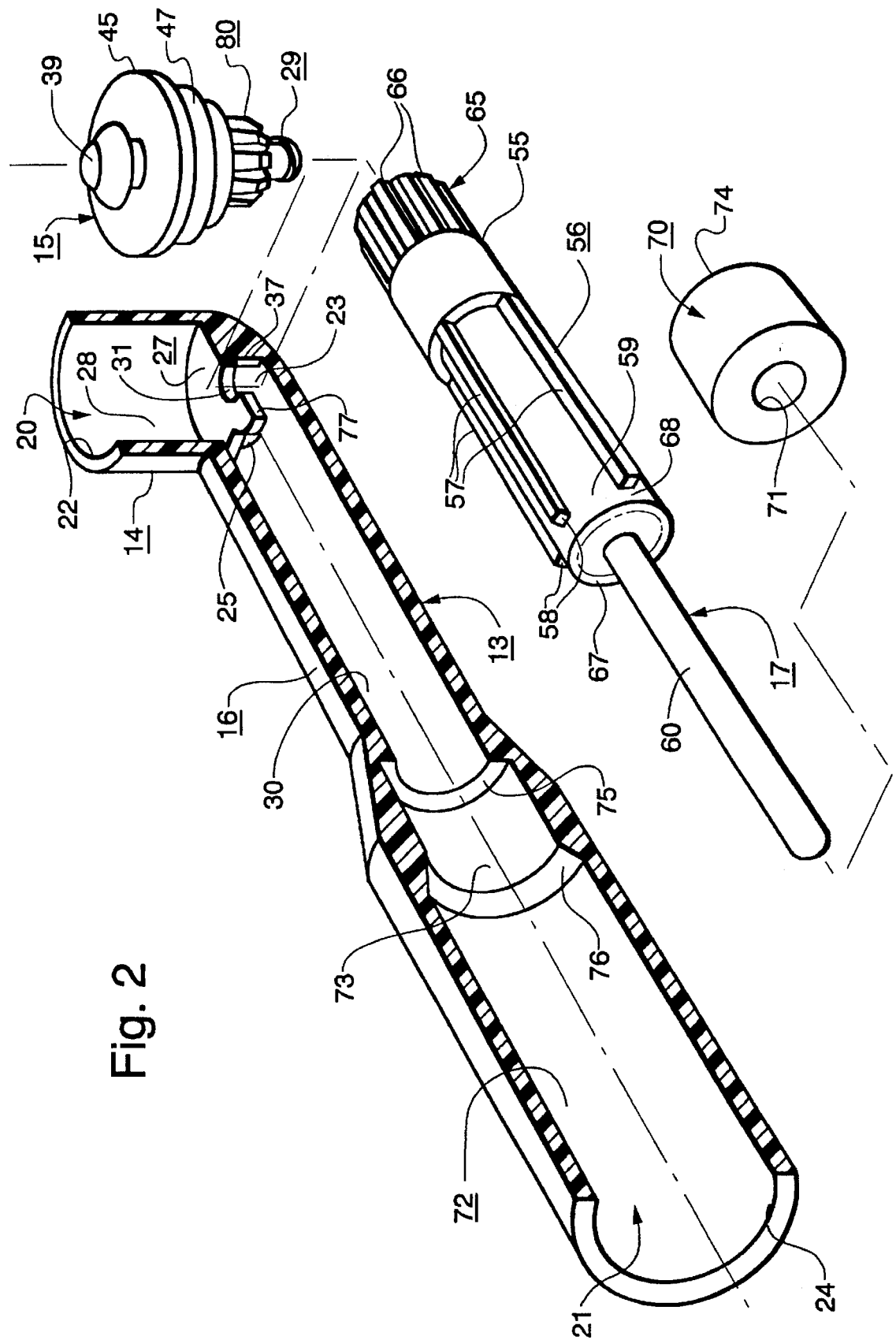
FIG. 2 is an exploded perspective view of the prophy angle of FIG. 1.

Turning next to a consideration of the details of the elongated drive shaft 17 in the passageway 21 attention is drawn to both FIG. 1 and FIG. 2. A number of important features of the present invention in one of its important aspects are shown that reduced friction which is one of the very important overall objective of the present invention. The elongated drive shaft 17 has an enlarged cylinder portion or hub 55 and a section 56 of vanes 57 having feet 58. The feet are positioned at the outer dimension of the circumference of the hub. In other words the flutes 59 between the vanes 57 and the feet 58 provide a considerable reduction in the frictional drag as against having the hub 55 continue longitudinally the length of the vane section 56. However, stability is provided against wobbling or bending, buckling or even breaking that might occur without the feet engaging the walls of the small bore 30 of the passageway 21. The vanes projecting outwardly from the center of the drive shaft to within about 0.002 inch of the surface circumference of the hub and extend linearly with the drive shaft. The vanes and the hub center the drive shaft for low friction rotation in the bore of the dental prophylaxis angle. The slight diminutin or reduction in the outward projection of the vanes reduces the area of interfacing contact with its resultant frictional drag on the inside of the bore 30 while still providing the desired stable rotation. The unsupported distance traversed by the thin driven shaft 60 which is coupled with the handpiece is not as great. To further reduce friction a rim 67 may be provided at the end of the barrel 68 of the drive shaft 17 that carries the vanes 57. However, for reasons of manufacture in some preferred embodiments rim 67 is omitted. At the opposite end of the drive shaft is the driving gear connection end 65 of the elongated drive shaft 17 with driving gears 66.

A locking sleeve 70 fits over the smaller connection shaft 60. The sleeve 70 is sized for a very tight press fit frictional engagement in the larger bore 72 of the housing. The inside large bore 72 of the bore of housing 16 is sized so that it constitutes a collar retainer portion 73. It has been found that with a sleeve length of preferably 0.183 to 0.191, more preferably 0.186 to 0.188 inch there is the right amount of friction with a bore diameter of preferably 0.272 to 0.276, more preferably 0.273 to 0.275 inch and a sleeve diameter of preferably 0.283 to 0.285, more preferably 0.284 to 0.285 inch to allow a tight press fit that will retain the drive gear 17 in position during the entire period of operation required for a complete and thorough prophylactic tooth cleaning in the dental operatory. The area of contact between sleeve 70 and collar retainer portion 73 should be preferably between 0.0115 and 0.0122, more preferably 0.0121 and 0.0122 square inch for best balance of results of ease of assembly and reliable sustained fit. The sleeve 70 bearing face 74 is stopped in its fully seated position by abutment wall 75. Preferable the bore 71 of the sleeve 70 is enough larger than the shaft 60 to prevent frictional engagement during operation from the driving means connection end of smaller shaft 60.

The drive shaft 17 has a bearing rim 67 which bears against and frictionally engages the bearing face 74 of the locking sleeve 70 during operation. A very small amount of loose play is allowed to keep the gears 65 and 80 engaged without binding of the parts because they are clamped or squeezed together. To assure the gear 65 does not move out of centered position the shaft 29 has a slight rounded extension 77 (FIG. 2) that engages loosely in an indentation 78 (FIG. 1) in the inner most tip of long driving gear 17. This construction has been found not to develop excess heat during operation.

Turning next to consideration of the provision of the driving connection between the driving gear 65 on the elongated drive shaft 17 and the driven gear 80 of the rotor 15, attention is again directed to both FIG. 1 and FIG. 2. The driving gear 65 is remote from the driving means, dental handpiece 12, connection end of the elongated drive shaft 17. The driven gear 80 is intermediate the end mounting attachment member 29 and the cup attaching area 39 of the rotor 15. The driving gear 65 and driven gear 80 mesh in the mounting and connection section of the gross housing 13 as shown in FIG. 1 with the driving gear 65 accessing the housing 14 from its side and from the housing 16 through the opening 25. This provides a driving connection of the driving gear 65 and the driven gear 80.

A prophy cup (not shown) or other dental tool is engaged on the prophylaxis tool mounting portion 39 of the tool rotation member rotor 15 in conventional manner. Other means of attaching prophy cups are known and this is not a part of the present invention. In some preferred embodiments, dental tools could be made as an integral part of the rotor 15.

Turning now to the engagement of the dental handpiece 12 which powers the prophy angle with the prophy angle, attention is called to FIG. 1. The passageway and the driving means connection end of the drive shaft will accept a variety of dental handpieces, although only one type is shown for purposes of illustration. The smaller shaft 60 of the drive shaft 17 is engaged by a dental handpiece in conventional manner well known in the dental profession. The handpiece nose is then advanced in the preferred configuration illustrated until the nose is engaged with the wedge restricting area 76 of the housing 16. The wedge 76 and housing opening 24 and adjacent bore are sized to match expeditiously with many dental handpiece noses. The rotatable driving gear shaft 17 is driven by the dental handpiece 12 mounted in the housing's bore.

In the course of manufacture, the housing 13, the drive shaft 17, and the driven member 15 will preferably be injection molded plastic with the housing being formed preferably of polyester (Celanex 2002-3 product of Celanese Hoechst Corp.), the drive shaft acetal copolymer (Celcon MC270HM product of Celanese Hoechst Corp.) and the driven rotor member Nylon mineral filler and short glass fibers (Minlon 22C nylon a product of Dupont). The locking sleeve 70 is preferably constructed of a material suitable as an excellent bearing member such as nylon to aid to low friction rotation. The material used was Nylon 66 natural (a product of Dupont).

It has been found advantageous to provide the same gear parameters as described in U.S. Pat. No. 5,040,978, which is incorporated herein by reference.

To mold the housing 13 it will be understood that it is very much preferred to have the attachment retainer housing part or strut 27 in line with both passage 21 and passage 20 to enable the withdrawal of the core pins. It is also preferable to have a small vent hole 81 in the housing 13 to secure the core pin in position and reduce flash. A vent hole 81 is left by a mold support pin. The vent hole is positioned and blocked closed by the hub 55 which is sized to a preferred circumference with a diameter of about 0.224, more preferably about 0.225 inch which provides a clearance on each side of about 0.0005 to 0.005, more preferably about 0.0005 to 0.0025 inch wih the bore wall overlying it and positioned longitudinally on said drive shaft in alignment with the vent hole, closing the vent hole opening to the interior of the bore. This positioning substantially reduces and in most cases eliminates the pumping in or out of saliva, debris and moisture of prior constructions caused by the rotating gears acting like a gear pump to pressure either side. The hub has a linear dimension of about 0.18 to 0.22, more preferably 0.19 to 0.21 inch in the direction of its axis.

After the parts have been molded and cleaned up to remove any flash and the like, several dabs of silicone lubricant (Novagard silicone G-661) are applied at the entrance to bore 30 from end 24. A small quantity of the silicone lubricant is also applied to each end of the hole 31. Then the driving shaft 17 is inserted into passageway 21. Next the locking sleeve 70 is inserted into the passageway 21 with the bore 71 receiving the small shaft 66 of the long gear. The end of the locking sleeve which will become the bearing surface 74 is thereby brought into engagement with the bearing surface 67 on the long gear 17. The locking sleeve 70 is press fit firmly all the way into position against wall 75 of housing 16.

The stud that is the shank or projection 15 and boss 50 are inserted into the hole or eyelet 31 with the boss or head 50 being forced through, deforming as it passes through and then extending to permanently mount the driven member 15 within the housing against accidental separation. Thereafter the driven prophy cup (not shown) is snapped over stud 39 on the short gear mounting member 15. The completed prophy angle is then packaged. Of course, the prophy cups can be supplied separately.

To operate the prophy angle, an angle is positioned on a handpiece as shown in FIG. 1 and the prophy cup is loaded with prophy paste by a dental professional in the dental operatory. Then a dental patient is provided with prophylaxis treatment in the usual manner. Of course the prophy cup is usually refilled with prophy paste from time to time. At the end of a prophylaxis treatment the prophy angle should be disposed of in an environmentally approved manner. It is intended that the prophy angle of this invention only be used on a single patient and then discarded.

It will be obvious to those skilled in the art that various changes and modifications may be made in the invention without departing from its true spirit and scope. It is, therefore, aimed in the appended claims to cover all such equivalent variations as fall within the true spirit and scope of the invention.

What is claimed is:

1. A dental prophylaxis angle of the type having the shaft of a tool mounting member journaled in a strut in the dental prophylaxis angle's housing, the mounting member having been mounted by passing an enlarged portion at its outer end sized to require forcible insertion through a hole in the strut, the enlarged portion having at least one camming surface to aid passage through said hole and at least one mating retaining surface that is not tapered toward said hole after insertion through said hole whereby said prophylaxis tool mounting member is permanently retained against withdrawal when mounted through said hole in the strut with said retaining surface and at least one mating retaining surface on said strut in mating engagement, the improvement comprising:

said shaft having a journaled shaft portion having a first circumference and said at least one camming surface of said enlarged portion comprising at least one lateral extension projecting laterally beyond said first circumference a greater distance than portions of said outer end of said shaft circumferentially adjacent thereto.

2. The dental prophylaxis angle of claim 1 wherein said housing has an open end with a central axis and said hole in said strut is aligned with said central axis and said enlarged portion comprising at least two lateral extensions substantially opposed to one another circumferentially, their camming surfaces balanced thereby, substantially aiding in aligning and maintaining the alignment of said tool mounting member with the axis of said open end as said enlarged portion is forcibly inserted through said hole in said strut.

3. The dental prophylaxis angle of claim 2 wherein said extensions consist essentially of two opposed lobes that together form a substantially even oval in a plane perpendicular to the axis of said shaft and at the oval's narrowest lateral dimension having a diameter substantially equal to the diameter of said journaled shaft portion.

4. The dental prophylaxis angle of claim 3 wherein each of said opposed lobes projects about 0.0045 to 0.008 inch from the circumference of the shaft at the lobes greatest extension and said oval diameter substantially equal to the diameter of the journaled shaft at its narrowest diameter lateral dimension is about 0.088 to 0.090 inch.

5. The dental prophylaxis angle of claim 4 wherein said outer end of said shaft is substantially evenly served and is substantially a half circle taken in cross section at its greatest projection.

6. The dental prophylaxis angle of the type having a plastic housing containing a bore having a predetermined inside circumference, a vent hole through a wall of said housing opening to the interior to said bore, and a rotatable driving gear shaft driven by a dental handpiece mounted in said bore, comprising:

said driving gear shaft comprising a hub sized to a circumference providing a clearance of about 0.0005 to 0.0025 inch with the said circumference of said bore and positioned longitudinally on said drive shaft in alignment with said vent hole, closing said vent hole opening to the interior of said bore.

7. The dental prophylaxis angle of claim 6 wherein said hub has a linear dimension of about 0.19 to 0.21 inch.

8. The dental prophylaxis angle of claim 7 wherein said drive shaft has a plurality of vanes projecting outwardly from the center thereof to within about 0.002 inch of the circumference of said hub and extending linearly with said drive shaft, said vanes and said hub centering said drive shaft for low friction rotation in said bore.

9. The dental prophylaxis angle of claim 6, wherein said plastic housing comprising a second bore having a greater circumference than the first said bore, outwardly from the first bore and aligned with said first bore, a relatively perpendicular wall joining said first bore and said second bore; said rotatable driving gear shaft comprising a second hub of lesser circumference than said first hub and extending on said driving gear shaft on the other side of said vanes from said first hub, an outer end of reduced circumference from said second hub and driving gears on said driving gear shaft at its inner end; a locking sleeve comprising an outer cylinder, two oppositely facing walls at the opposite sides of said outer cylinder and a central hole, said outer cylinder sized to form a tight locking frictional fit when forced into said second bore and said central hole sized to allow said outer end of said driving gear shaft to pass through said locking sleeve without touching said locking sleeve, said first bores length being proportioned to position said relatively perpendicular wall to hold said driving gears in operable position when said locking sleeve locks said driving gear shaft in position.

* * * * *